United States Patent [19]

Reinbold et al.

[11] 3,998,700

[45] Dec. 21, 1976

[54] CULTURE MEDIUM AND METHOD OF PREPARING BULK STARTERS FOR ITALIAN CHEESE MANUFACTURE

[75] Inventors: George W. Reinbold, Wheat Ridge; Malireddy S. Reddy, Thornton, both of Colo.

[73] Assignee: Leprino Cheese Co., Denver, Colo.

[22] Filed: Aug. 27, 1975

[21] Appl. No.: 608,094

[52] U.S. Cl. .................................. 195/96; 195/100; 426/36; 426/41; 426/43; 426/61
[51] Int. Cl.² ........................................ C12K 3/00
[58] Field of Search .................... 195/96, 111, 100; 426/34, 41, 42, 43, 56, 61, 583, 36, 55, 39

[56] References Cited

UNITED STATES PATENTS 3,531,297 9/1970 Kielsmeier et al. .................. 426/36
3,852,158 12/1974 Anderson et al. ............... 426/36 X

*Primary Examiner*—R. B. Penland
*Attorney, Agent, or Firm*—Tilton, Fallon, Lungmus, Chestnut & Hill

[57] ABSTRACT

Bulk starters having optimized ratios of coccus (*Streptococcus thermophilus*) to rod (lactobacilli) bacteria are prepared in a whey-based culture medium characterized by defined proportions of acid-whey solids to sweet-whey solids, the sweet-whey preferably being partially delactosed whey. The medium and method are particularly adapted for use in manufacturing *pasta filata* cheeses.

18 Claims, No Drawings

CULTURE MEDIUM AND METHOD OF PREPARING BULK STARTERS FOR ITALIAN CHEESE MANUFACTURE

BACKGROUND AND PRIOR ART

In the manufacture of Italian cheese, such as Mozzarella, the milk in the cheese vat is inoculated with from approximately 2 to 4% of a bulk starter providing a mixed culture of the acid-forming organisms. In the manufacture of Mozzarella and other *pasta filata* cheeses, it is the practice to employ *Streptococcus thermophilus* together with one or more lactobacilli. Streptococci are referred to by the short name of "coccus" while the lactobacilli are referred to as "rod" bacteria because of their appearance under microscopic examination. The preferred ratio of coccus to rod cells in Italian cheese starters is from about 3:1 to 5:1. Cheesemakers have difficulty in maintaining this ratio in bulk starters, as prepared in the plant, even though culture manufacturers supply concentrates in ratios near those normally desired. Certain variations in these optimum ratios can be tolerated within the skill of the art while still producing acceptable quality cheese, but the flavor and physical properties of the cheese, such as elasticity, "stringiness," flavor, and moisture may be seriously affected unless both coccus and rod organisms are present and growing actively. To assure this, bulk starters as added to the cheese vats should at least have a coccus to rod ratio within the range from 2.5:1 to 5.5:1.

In an older practice, which has been largely abandoned by present United States cheese manufacturers, fresh whey from prior vats of Italian cheese was used as a culture medium to produce the bulk starter. Such use of liquid whey saved from previously made vats of cheese is a hazardous practice. Inhibitory compounds, heat-resistant contaminating bacteria, and equally heat-resistant bacteriophage may be present in the whey. Consequently, under present-day manufacture conditions in the United States, the culture media for preparing Italian cheese bulk starters comprises reconstituted non-fat dry milk (NFDM) singly or in combination with various levels of sweet-whey. Reconstituted NFDM is an expensive cultue medium because of the high price of non-fat dry milk. It is the medium of choice, however, because it is a dependable material which can be pretested. It would be very desirable to find a much less expensive culture medium for producing Italian cheese bulk starters with the proper coccus to rod ratios, which medium would be as dependable, safe, and subject to pretesting as NFDM-based media.

Attempts have been made to develop whey-based media for preparation of bulk starters, for the manufacture of cheese, including Italian cheeses. Both fresh whey and reconstituted dried sweet-whey have been used. U.S. Pat. No. 2,805,950 describes the preparation of bacterial cultures for use in the making of Swiss cheese. *Streptococcus thermophilus* either alone or in combination with lactobacilli are cultured in whey, such as fresh whey from a prior Swiss cheese making operation, and after completion of the culturing, from 5 to 15% of milk powder is added, and the incubated culture is frozen to be held for future use. As recognized in this patent (col. 3, line 61, et seq.), a major problem in making Swiss cheese has been in obtaining the proper coccus to rod proportions. The patent recommends preparation of pure cultures of coccus (*S. thermophilus*) and separate pure cultures of rods (lactobacilli), which are then mixed in the proper proportions for use in the cheese vats. Preferably, therefore, the process of the patent involves the cultivation in a whey culture of *Streptococcus thermophilus* substantially free from lactobacilli.

U.S. Pat. No. 3,852,158 describes a bulk starter medium, which can be prepared in dry form, from milk products or derivatives including sweet-whey, NFDM, acid-whey powder, buttermilk powder, whole-milk powder, and mixtures thereof. One preferred formulation contains a major amount of sweet-whey and a minor amount of NFDM. The culture media is characterized by containing citrate. It is recommended for use in preparing a wide variety of cheese starter cultures.

Cottage, Swiss, and Italian bulk culture manufacture with a whey-based bacteriophage inhibitory medium under pH control is described by W.L. Chen and G.H. Richardson, *J. Dairy Sc.*, Vol. 58, No. 5, pp. 785-786. Both acid-whey and sweet-whey were tested but not in combination.

During the experimental work leading to the present invention, it was found that neither reconstituted dried sweet-whey or reconstituted dried acid-whey were satisfactory media for producing Italian cheese bulk starters. Acid-whey inhibits the growth of both the coccus and rod bacteria. With sweet-whey, the lactobacilli are inhibited with the result that the ratio of coccus to rod is much greater than desired. Partially delactosed sweet-whey results in even greater disparities in the desired coccus to rod ratios, the coccus growing profusely while the rods grow poorly. None of these whey media are, therefore, comparable to reconstituted NFDM for the production of Italian cheese bulk starters.

SUMMARY OF INVENTION

This invention is based in part on the discovery that for use as an Italian cheese bulk starter medium reconstituted sweet-whey, either natural or partially delactosed, must be combined with a critical amount of acid-whey solids. The necessary proportions for optimum results are within the range from 10 to 30 parts by weight of acid-whey solids to 70 to 90 parts by weight of sweet-whey solids. For maintaining optimized ratios of coccus to rod cells in the bulk starters, from 15 to 25 parts by weight of acid-whey solids are combined with 75 to 85 parts of sweet-whey solids. Further, the sweet-whey solids are preferably partially delactosed. With culture media formulated in this manner, as good or better results are obtained as when the culture medium constitutes 100% reconstituted NFDM. Although a minor amount of NFDM solids can be combined with the mixture of acid- and sweet-whey solids, the preferred formulations of this invention do not contain NFDM and are composed substantially entirely of acid-whey solids and sweet-whey solids in the specified proportions.

Media prepared in accordance with the present invention are particularly advantageous for preparing starter cultures for manufacturing *pasta filata* cheeses, such as Mozzarella, Provolone, Caciocavallo, and other stretched curd cheeses. For all of these cheeses, it is advantageous to prepared mixed coccus and rod cultures. In addition, media prepared in the same manner, may be advantageous for cultivation of rod and coccus cultures, as grown separately, for certain other cheeses, such as Swiss cheese.

Detailed Description

Whey is the food obtained as a fluid by separation of the coagulum from milk, cream, or skim milk. It is one of the principal by-products of cheese manufacture. Dry whey is prepared by removing the moisture from natural whey. It contains the lactose, protein, and mineral constituents in the same relative proportions as in whey. Whey may also be modified, such as by partial removal of the lactose. As generally accepted in the cheese and whey industry, partially delactosed whey has a lactose content which does not exceed 60% of the whey solids.

In general, there are two types of whey. One of these is known as "sweet" whey and the other as "acid" whey. Sweet-whey is obtained as a by-product of manufacturing most cheese, such as Cheddar, Swiss, and Mozzarella. Acid-whey is obtained primarily as a by-product of Cottage cheese manufacture. As generally accepted in the cheese and whey industry and for the purpose of the present application, acid-whey is whey, in either liquid or dry form, which has a titratable acidity of not less than 0.30%. Typically, the acidities of acid-type wheys range from around 0.35 to 0.44%, while those of sweet-type wheys range from about 0.07 to 0.20.%. In general, it can be stated that sweet-whey has a titratable acidity of not more than 0.16%. Sweet-whey may be liquid, dry, or modified, such as partially delactosed whey. The preferred ingredients for formulating the culture medium of the present invention are dried acid-whey and dried sweet-whey, particularly dried partially delactosed sweet-whey.

In accordance with the present invention, a culture medium in dry form ready for reconstitution by addition of water is prepared by blending from 10 to 30 parts by weight of dry acid-whey solids with from 70 to 90 parts by weight of other solids selected from sweet-whey solids and mixtures thereof with non-fat dry milk (NFDM) solids. The amount of NFDM solids is limited to not over 1 part by weight per each 3 parts of total acid- and sweet-whey solids. In preferred formulations, the NFDM solids are omitted all together, or limited to not over 1 part by weight per each 9 parts of total acid- and sweet-whey solids.

More specifically, a culture medium for preparing mixed coccus and rod bulk starters for Italian cheese manufacture, in accordance with the present invention, consists essentially on a dry weight basis of 10 to 30% acid-whey solids having a titratable acidity of not less than 0.30%, and from 70 to 90% of other solids selected from sweet-whey solids or mixtures thereof with NFDM solids, the NFDM solids being limited in amount as previously described. In the preferred formulations from 15 to 25% of acid-whey solids are combined with 75 to 85% of the other solids, principally the sweet-whey solids, with not over 1 part by weight of NFDM solids present per 9 parts of total acid and sweet-whey solids.

The sweet-whey solids employed in the formulations of the present invention preferably have a titratable acidity of not over 0.16%. Particulary good results are obtained with partially delactosed dry sweet-whey solids, which contain not over 60% lactose on a dry weight basis. Partially delactosed dried wheys also contain relatively larger proportions of inorganic salts, referred to as minerals or ash. The preferred sweet-wheys, being partially delactosed wheys, contain from 15 to 25% minerals (ash) on a dry solids basis. Typically, the preferred partially delactosed dry sweet-whey for use in the present invention contains from 45 to 55 % lactose, from 20 to 25% whey protein, and from 15 to 25% minerals (ash).

The bulk starter dry mix, prepared as described, is employed in a manner similar to that of NFDM media. It is reconstituted with water to form an aqueous fermentation broth containing from 9 to 15% total solids. The preferred solids content is from 10 to 14%, with the optimum being around 11 to 12%. The fermentation broth is then inoculated with a mixed starter containing the *Streptococcus thermophilus* (coccus) and one or more heat resistant lactobacilli (rods). The ratio od coccus to rod cells should be within the range from 2.5 to 1 up to 5.5 to 1. Optimized ratios for manufacture of Mozzarella and similar Italian cheese are from about 3:1 to 5:1 coccus to rod cells. Such ratios are determined by microscopic examination and cell count, in accordance with the usual cheese microbiological practice.

Heat-resistant lactobacilli desirable for use in combination with *Streptococcus thermophilus* are members of the sub-genus *Thermobacterium* of the genus Lactobacillus. They include the species *L. caucasicus*, *L. lactis*, *L. helveticus*, *L. acidophilus* and *L. bulgaricus*. For preparation of Mozzarella cheese, mixtures of *S. thermophilus* and *L. bulgaricus* are particularly desirable. Other desirable lactobacilli are *L. helveticus* and *L. lactis*.

For practicing the present invention, a particularly advantageous formulation consists of 20% by weight dried acid whey, such as dried Cottage cheese whey, uniformly blended with 80% of dried partially delactosed sweet-whey. Such products are commerically available in the United States from a number of companies. One suitable partially delactosed whey is sold under the name "Puritein 20" by the Purity Cheese Company of Mayville, Wisconsin. This product is partially delactosed whey made by crystallization and partial separation of lactose from condensed whey. A representative formulation supplied by the manufacturer is lactose 50%, protein 22%, and ash 21%. Other modified wheys, which are partially delactosed, may also be partially demineralized. For example, the Puritein 25, (the product of Purity Cheese Company sold as "Puritein 25") is modified with respect to both lactose and mineral content. A typical formulation supplied by the manufacturer is lactose 52%, ash 14%, and protein 25%. As previously indicated, higher ash contents are desirable, such as ash contents in the range of 15 to 25% on a weight basis. However, Puritein 25 can be employed either alone, or in admixture with Puritein 20, or dried sweet-whey.

In accordance with known practice, the growth of the lactobacilli, such as *L. bulgaricus*, may be promoted by incorporating manganese ions in the fermentation broth. The water used for reconstitution of the dry mix may advantageously contain from 1 to 10 ppm $Mn^{++}$. The manganese may be added in the form of a non-toxic salt, such as manganous chloride. It will be understood, however, that for purpose of the present invention, such manganese addition is optional, as is the incorporation of other accessory growth factors, such as yeast extract, corn steep liquor, etc.

Experimental Comparisons

Media prepared in accordance with the present invention were compared with other media, including reconstituted NFDM, sweet-whey, and delactosed whey. All dry media were reconstituted to 12% solids with distilled water. (In the plant, pretested tap water would be used to insure the absence of inhibitory compounds.) Three different starter cultures were used, as identified below. Incubation temperatures were in accordance with usual procedures, such as temperatures of from 100 to 108° F. which favored the growth of the particular bacteria. The fermentation times ranged from 7 to 16 hours, starting with an initial broth pH above 6.0, such as 6.3 to 6.5, and continuing to a final pH below 4.8 and usually below 4.5.

In the following experiments the material referred to as "Pur-20" is Puritein 20, a partially delactosed whey sold by the Purity Cheese Company, having a typical analysis of lactose 50%, protein 22%, and ash 21%. This material is supplied in the form of a dry powder. The material referred to as acid whey was dry whey produced as a by-product of Cottage cheese manufacture having an approximate percent titratable acidity of 0.39%. The material referred to as sweet-whey was dry sweet-whey having th approximate analysis 70% lactose, 13% protein, and 8% ash.

Experiment 1

Four media comprising the mixtures of sweet-whey and acid-whey formulated in accordance with the present invention were compared with three other media. The liquid fermentation broths were prepared as described above from the dry ingredients, and the broth was inoculated with a mixed culture of *S. thermophilus* and *L. bulgaricus* having a ratio of coccus to rod cells of approximately 4:1. The amount of this culture added to the broth was 1% by weight. The incubation temperature for all tests was 106° F. The progress of the fermentation was followed by measuring titratable acidities, bacterial activities, and coccus to rod ratios. The data are reported below in Tables 1-A, 1-B, and 1-C, wherein the media are identified by code letters A to G, which refer to the following formulations or materials.

| Medium | Composition* |
|---|---|
| A | Pur-20 (80 parts) + acid-whey (20 parts) |
| B | Pur-20 (80 parts) + acid-whey (20 parts) + 0.1% yeast extract + 0.2% corn steep liquor |
| C | Pur-20 (80 parts) + acid-whey (20 parts) + 0.1% yeast extract + 0.2% corn steep liquor + 0.25% dextrose |
| D | Sweet-whey (80 parts) + acid-whey (20 parts) |
| E | Non-fat dry milk |
| F | Sweet-whey |
| G | Pur-20 |

*(Formulated to 12% solids)

Table 1-A

Titratable Acidity and pH

| Medium | 7 | 9 | Hours 12 | 14 | 16 | 20 |
|---|---|---|---|---|---|---|
| A | 0.780* | 0.850 | 1.070 | 1.200 | 1.410 | 1.410 |
|   | (4.80)** | (4.60) | (4.60) | (4.30) | (4.15) | (4.30) |
| B | 1.050 | 1.190 | 1.320 | 1.400 | 1.470 | 1.510 |
|   | (4.35) | (4.35) | (4.30) | (4.15) | (4.10) | (4.25) |
| C | 1.010 | 1.220 | 1.320 | 1.400 | 1.470 | 1.520 |
|   | (4.35) | (4.30) | (4.30) | (4.15) | (4.10) | (4.00) |
| D | 0.700 | 0.810 | 0.910 | 0.990 | 1.050 | 1.160 |
|   | (4.60) | (4.40) | (4.30) | (4.15) | (4.05) | (4.20) |
| E | 1.160 | 1.330 | 1.450 | 1.500 | 1.570 | 1.650 |
|   | (4.00) | (4.00) | (3.85) | (3.80) | (3.75) | (3.95) |
| F | 0.290 | 0.360 | 0.470 | 0.570 | 0.640 | 0.730 |
|   | (5.80) | (5.70) | (5.30) | (5.00) | (4.90) | (4.60) |
| G | 0.550 | 0.720 | 0.820 | 0.910 | 0.910 | 1.030 |

Table 1-A-continued

Titratable Acidity and pH

| Medium | 7 | 9 | Hours 12 | 14 | 16 | 20 |
|---|---|---|---|---|---|---|
|   | (5.55) | (5.35) | (5.00) | (4.80) | (4.90) | (4.85) |

*Developed acidity (% titratable acidity)
**pH

Table 1-B

Activity Test Results

| Medium | 7 | 9 | Hours 12 | 14 | 16 | 20 |
|---|---|---|---|---|---|---|
| A | 0.840 | 0.870 | 0.840 | 0.800 | 0.700 | 0.670 |
| B | 0.890 | 0.890 | 0.830 | 0.790 | 0.689 | 0.530 |
| C | 0.930 | 0.860 | 0.815 | 0.755 | 0.690 | 0.530 |
| D | 0.930 | 0.885 | 0.825 | 0.780 | 0.625 | 0.510 |
| E | 1.000 | 0.920 | 0.840 | 0.525 | 0.470 | 0.460 |
| F | 0.530 | 0.580 | 0.630 | 0.650 | 0.560 | 0.500 |
| G | 0.620 | 0.610 | 0.630 | 0.610 | 0.560 | 0.480 |

Table 1-C

Coccus: Rod Ratios
(S. thermophilus: L. bulgaricus)

| Medium | 7 | 9 | Hours 12 | 14 | 16 | 20 |
|---|---|---|---|---|---|---|
| A | 5:1 | 4:1 | 4:1 | 4:1 | 4:1 | 3:1 |
| B | 5:1 | 4:1 | 4:1 | 3:1 | 3:1 | 3:1 |
| C | 4:1 | 4:1 | 3:1 | 3:1 | 3:1 | 3:1 |
| D | 3:1 | 3:1 | 2:1 | 2:1 | 2:1 | 1:1 |
| E | 3:1 | 3:1 | 1:1 | 1:1 | 1:1 | 1:1 |
| F | 60:1 | 60:1 | 20:1 | 5:1 | 5:1 | 4:1 |
| G | 80:1 | 80:1 | 60:1 | 20:1 | 10:1 | 5:1 |

Experiment 2

The same procedure was followed as in Example 1, except that the inoculant contained *L. helveticus* instead of *L. bulgaricus*. The incubation temperature was 106° F. The same measurements were made, and the data is reported below the Tables 2-A, 2-B, and 2-C, where the media are futher indentified as follows:

| Medium | Composition* |
|---|---|
| A | Pur-20 (80 parts) + acid-whey (20 parts) |
| B | Pur-20 (80 parts) + acid-whey (20 parts) + 0.75% yeast extract |
| C | Sweet-whey (80 parts) + acid-whey (20 parts) |
| D | Sweet-whey (80 parts) + acid-whey (20 parts) + .075% yeast extract |
| E | Non-fat dry milk |
| F | Sweet-whey |
| G | Pur-20 |

*(Formulated to 12% solids)

Table 2-A

Titratable acidity

| Medium | Hours 7 | 9 |
|---|---|---|
| A | 0.450* | 0.580 |
|   | (4.90)** | (4.70) |
| B | 0.525 | 0.645 |
|   | (4.80) | (4.70) |
| C | 0.400 | 0.535 |
|   | (5.00) | (4.70) |
| D | 0.480 | 0.630 |
|   | (4.90) | (4.60) |
| E | 0.415 | 0.520 |
|   | (5.30) | (5.05) |
| F | 0.005 | 0.005 |
|   | (7.50) | (7.50) |
| G | 0.155 | 0.300 |

Table 2-A-continued

Titratable acidity

| Medium | Hours 7 | 9 |
|---|---|---|
| | (6.30) | (5.90) |

*Developed acidity.
**pH

Table 2-B

Activity Test Results

| Medium | Hours 7 | 9 |
|---|---|---|
| A | 0.520 | 0.540 |
| B | 0.525 | 0.550 |
| C | 0.500 | 0.505 |
| D | 0.525 | 0.545 |
| E | 0.430 | 0.420 |
| F | 0.200 | 0.210 |
| G | 0.370 | 0.375 |

Table 2-C

Coccus: Rod Ratios
(S. thermophilus: L. helveticus)

| Medium | Hours 7 | 9 |
|---|---|---|
| A | 6:1 | 3:1 |
| B | 3:1 | 3:1 |
| C | 4:1 | 2:1 |
| D | 3:1 | 2:1 |
| E | 19:1 | 16:1 |
| F | 1:0 | 1:0 |
| G | 1:0 | 1:0 |

Experiment 3

The same procedure as in Experiments 1 and 2 was followed, except that the innoculum contained L. lactis as the rod bacteria. The incubation temperature was 106° F. The media are identical to those used in Experiment 2, and the letter identifications refer to the same media as in Experiment 2. The data is reported below the Tables 3-A, 3-B, and 3-C.

Table 3-A

Titratable Acidity and pH.

| Medium | Hours 7 | 9 |
|---|---|---|
| A | 0.495* | 0.700 |
| | (5.00)** | (4.70) |
| B | 0.650 | 0.850 |
| | (4.70) | (4.50) |
| C | 0.595 | 0.875 |
| | (4.70) | (4.40) |
| D | 0.700 | 0.885 |
| | (4.70) | (4.35) |
| E | 0.005 | 0.005 |
| | (7.50) | (7.50) |
| F | 0.195 | 0.385 |
| | (6.30) | (5.60) |
| G | 0.460 | 0.670 |
| | (4.90) | (4.50) |

*Developed acidity.
**pH

Table 3-B

Activity Test Results

| Medium | Hours 7 | 9 |
|---|---|---|
| A | 0.525 | 0.575 |
| B | 0.580 | 0.595 |
| C | 0.540 | 0.525 |
| D | 0.530 | 0.540 |
| E | 0.200 | 0.200 |

Table 3-B-continued

Activity Test Results

| Medium | Hours 7 | 9 |
|---|---|---|
| F | 0.340 | 0.405 |
| G | 0.460 | 0.440 |

Table 3-C

Coccus: Rod Ratios
(S. thermophilus: L. lactis)

| Medium | Hours 7 | 9 |
|---|---|---|
| A | 6:1 | 3:1 |
| B | 3:1 | 3:1 |
| C | 1:1 | 1:1 |
| D | 7:1 | 3:1 |
| E | 1:0 | 1:0 |
| F | 1:0 | 1:0 |
| G | 1:1 | 1:1 |

In the foregoing experiments, the developed acidity, measured as percent of titratable acidity, was determined in accordance with standard preocedures. Nine grams of medium were weighed into a white porcelain cup. Ten drops of a 1.0% alcoholic solution of phenolphthalein were added and the mixture was titrated to a faint pink (30 second duration) endpoint with 0.1 N sodium hydroxide solution. After subtracting the uninoculated medium control titration, results were reported as percent developed acidity expressed as lactic acid.

The activity tests carried out as follows: One hundred millilters of autoclaved, pretested, 11% solids reconstituted NFDM were inoculated with 2 ml. of active mixed culture. The culture was then incubated at 33° C. (90° F.) for 45 minutes. At the end of this period, the temperature of the culture was slowly raised to 46° C. (115° F) in 30 minutes. The culture was then held at this final temperature for 2 hours. The % titratable acidity was determined as stated in the preceding paragraph.

The procedure for determining the coccus to rod ratios in the foregoing experiments was that of microscopic examination, the approximate ratio of coccos to rod cells being determined by visual counting. This is a standard procedure for monitoring the ratio of coccus to rod cells in cheese manufacture. One loopful of starter and one loopful of distilled water were mixed and distributed over 1 square centimeter on a clean slide. After fixing, the methylene blue-stained culture medium was viewed microscopically under an oil immersion objective. The total number of rods and cocci were counted in each of three different fields, totaled, and averaged. The results were expressed in terms of the coccus to rod ratio.

The results of the foregoing experiments can be summarized as follows: Neither reconstituted sweet-whey nor acid-whey solids alone function as effectively as starter media as either reconstituted NFDM or a properly proportioned mixture of sweet-whey and acid-whey solids. Further, partially delactosed sweet-whey solids when substituted for the sweet-whey solids in the mixture give even better results, supporting excellent growth of mixed rod and coccus cultures. This appears to be due to the inherent stimulation of the rod culture by the acid-whey plus the buffering action of the higher ash content of these mixtures. In general, favorable rod to coccus ratios are both attained and maintained by the starter media of this invention. It can therefore be seen that the invention provides an important advance in the art of preparing bulk starters for Italian cheese manufacture. The bulk starters prepared in accordance with the invention are as of good or better quality as those prepared from NFDM bulk starters, while being much less expensive to prepare. With respect to the media cost, and in relation to current market prices for NFDM, dry sweet-whey, dry acid-whey, and dry delactosed whey, the approximate savings can be expected to range from about 60 to 90% with respect to the whey-based media of this invention as compared with the standard NFDM medium.

We claim:

1. A culture medium consisting essentially on a dry weight basis of:
   a. 10 to 30% acid-whey solids having a titratable acidity of not less than 0.30%; and
   b. 70 to 90% of other solids selected from sweet-whey solids and mixtures thereof with non-fat dry milk (NFDM) solids, said milk solids being present is not over 1 part by weight per each 3 parts of total acid-whey and sweet-whey and solids.

2. A culture medium for preparing mixed coccus and rod bulk starters for Italian cheese manufacture, consisting essentially on a dry weight basis of:
   a. 15 to 25% acid-whey solids having a titratable acidity of not less than 0.30%; and
   b. 75 to 85% of other solids selected from sweet-whey solids and mixtures thereof with non-fat dry milk (NFDM) solids, said milk solids being present in not over 1 part by weight per each 9 parts of total acid-whey and sweet-whey solids.

3. The culture medium of claim 2 in which said other solids are composed substantially entirely of sweet-whey solids having a titratable acidity of not over 0.16%.

4. The culture medium of claim 2 in which said sweet-whey solids are partially delactosed sweet-whey solids containing not over 60% lactose on a dry weight basis.

5. A culture medium for preparing mixed coccus and rod bulk starters for Italian cheese manufacture, consisting essentially on a dry weight basis of:
   a. 15 to 25% of cottage cheese acid-whey solids having a titratable acidity of not less than 0.30%; and 75 to 85% of sweet-whey solids having a titratable acidity of not over 0.16%, said sweet-whey solids being partially delactosed sweet-whey solids containing not over 60% lactose on a dry weight basis.

6. The culture medium of claim 5 in which said sweet-whey solids contain from 15 to 25% minerals (ash) on a dry weight basis.

7. The culture medium of claim 5 in which said sweet-whey solids contain on a dry weight basis from 45 to 55% lactose, from 20 to 25% protein, and from 15 to 25% minerals (ash).

8. The method of preparing a mixed coccus and rod bulk starter for Italian cheese manufacture, comprising:
   a. preparing an aqueous fermentation broth containing from 9 to 15% total solids, said solids consisting essentially of 15 to 25% acid-whey solids having a titratable acidity of not less than 0.30% together with 70 to 90% of other solids selected from sweet-whey solids and mixtures thereof with non-fat dry milk (NFDM) solids, said milk solids being present in not over 1 part by weight per each 9 parts of total acid-whey and sweet-whey solids;
   b. inoculating said broth with a mixed starter containing *Streptococcus thermophilus* (coccus) and Lactobacillus of the sub-genus Thermobacterium (rod) in the ratio of coccus to rod cells of from 2.5:1 to 5.5:1; and
   c. culturing said coccus and rod cells in said broth to produce a bulk starter containing a ratio of coccus to rod cells of from 2.5:1 to 5.5:1.

9. The method of claim 8 in which said Lactobacillus is *L. bulgaricus*.

10. The method of claim 8 in which said Lactobacillus is *L. helveticus*.

11. The method of claim 8 in which said Lactobacillus is *L. lactis*.

12. The method of preparing a mixed coccus and rod bulk starter for Italian cheese manufacture, comprising:
   a. preparing an aqueous fermentation broth containing from 10 to 14% total solids, said solids consisting essentially of 15 to 25% of cottage cheese acid-whey solids having a titratable acidity of not less than 0.30% together with 75 to 85% of sweet-whey solids containing not over 60% lactose and from 15 to 25% minerals (ash) on a dry weight basis;
   b. inoculating said broth with a mixed starter containing *Streptococcus thermophilus* (coccus) and Lactobacillus of the sub-genus Thermobacterium (rod) in the ratio of coccus to rod cells of from 2.5:1 to 5.5:1; and
   c. culturing said coccus and rod cells in said broth to produce a bulk starter containing a ratio of coccus to rod cells of from 2.5:1 to 5.5:1.

13. The method of claim 12 in which said sweet-whey has a titratable acidity of not over 0.16% and contains on a dry weight basis from 45 to 55% lactose, from 20 to 25% protein, and from 15 to 25% minerals (ash).

14. The method of claim 12 in which said Lactobacillus is *L. bulgaricus*.

15. The method of claim 12 in which said Lactobacillus is *L. helveticus*.

16. The method of claim 12 in which said Lactobacillus is *L. lactis*.

17. The method of preparing a mixed coccus and rod bulk starter for Italian cheese manufacture, comprising:
   a. preparing an aqueous fermentation broth containing from 10 to 14% total solids, said solids consisting essentially of 15 to 25% cottage cheese acid-whey solids having a titratable acidity of not less than 0.30% together with 75 to 85% partially delactosed sweet-whey solids containing not over 60% lactose and from 15 to 25% minerals (ash) on a dry weight basis;
   b. inoculating said broth with a mixed starter containing *Streptococcus thermophilus* (coccus) and *Lactobacillus bulgaricus* (rod) in the ratio of coccus to rod cells of from about 3:1 to 5:1; and
   c. culturing said coccus and rod cells in said broth to produce a bulk starter containing a ratio of coccus to rod cells of from about 3:1 to 5:1.

18. A culture medium consisting essentially on a dry weight basis of:
   a. 15 to 25% of Cottage cheese acid-whey solids having a titratable acidity of not less than 0.30%; and
   b. 75 to 85% of other solids selected from sweet-whey solids and mixtures thereof with non-fat dry milk (NFDM) solids, said milk solids being present in not over 1 part by weight pre each 9 parts of total acid-whey and sweet-whey solids.

* * * * *

UNITED STATES PATENT AND TRADEMARK OFFICE
CERTIFICATE OF CORRECTION

PATENT NO. : 3,998,700
DATED : December 21, 1976
INVENTOR(S) : George W. Reinbold and Malireddy S. Reddy It is certified that error appears in the above-identified patent and that said Letters Patent are hereby corrected as shown below:

Col. 9, line 23 change "is" to in.

Col. 9, line 47 add b. prior to "75".

Col. 10, lines 2-3 italicize Lactobacillus.

Col. 10, line 3 italicize Thermobacterium.

Col. 10, line 9 italicize Lactobacillus.

Col. 10, line 11 italicize Lactobacillus.

Col. 10, line 13 italicize Lactobacillus.

Col. 10, lines 25-26 italicize Lactobacillus.

Col. 10, line 26 italicize Thermobacterium.

Col. 10, lines 36, 38 and 40 italicize Lactobacillus (in each appearance).

Col. 10, line 47 add "of" prior to "cottage cheese".

Col. 10, line 67 correct spelling of per.

Signed and Sealed this

Twenty-ninth Day of March 1977

[SEAL]

Attest:

RUTH C. MASON
Attesting Officer

C. MARSHALL DANN
Commissioner of Patents and Trademarks